(12) United States Patent
Noh et al.

(10) Patent No.: US 10,960,102 B2
(45) Date of Patent: Mar. 30, 2021

(54) SUPERABSORBENT POLYMER COMPOSITION

(71) Applicant: LG Chem, Ltd., Seoul (KR)

(72) Inventors: Wook Hwan Noh, Daejeon (KR); Jun Kyu Kim, Daejeon (KR); Jong Hyuk Kwon, Daejeon (KR); Young Jae Hur, Daejeon (KR); Ki Han Kim, Daejeon (KR)

(73) Assignee: LG Chem, Ltd.

(*) Notice: Subject to any disclaimer, the term of this patent is extended or adjusted under 35 U.S.C. 154(b) by 403 days.

(21) Appl. No.: 15/027,535

(22) PCT Filed: Dec. 11, 2014

(86) PCT No.: PCT/KR2014/012213
§ 371 (c)(1),
(2) Date: Apr. 6, 2016

(87) PCT Pub. No.: WO2015/088266
PCT Pub. Date: Jun. 18, 2015

(65) Prior Publication Data
US 2016/0235882 A1    Aug. 18, 2016

(30) Foreign Application Priority Data
Dec. 13, 2013 (KR) .................. 10-2013-0155597

(51) Int. Cl.
*A61L 15/60* (2006.01)
*C08L 101/14* (2006.01)
(Continued)

(52) U.S. Cl.
CPC .............. *A61L 15/60* (2013.01); *A61L 15/24* (2013.01); *C08L 101/14* (2013.01); *C08K 2003/2227* (2013.01); *C08L 33/04* (2013.01)

(58) Field of Classification Search
CPC ........ C08L 101/14; C08L 33/04; A61L 15/24; A61L 15/60; C08K 2003/2227
See application file for complete search history.

(56) References Cited

U.S. PATENT DOCUMENTS

| 4,446,261 A | 5/1984 | Yamasaki et al. |
| 4,587,308 A | 5/1986 | Makita et al. |

(Continued)

FOREIGN PATENT DOCUMENTS

| CN | 1528795 A | 9/2004 |
| CN | 1955201 A | 5/2007 |

(Continued)

OTHER PUBLICATIONS

International Search Report from PCT/KR2014/012213, dated Mar. 27, 2015.

(Continued)

Primary Examiner — Michael B Nelson
(74) Attorney, Agent, or Firm — Lerner, David, Littenberg, Krumholz & Mentlik, LLP

(57) ABSTRACT

A superabsorbent polymer which has excellent initial absorbency and keeps water from flowing out under pressure even after the passage of a long period of time, in which the superabsorbent polymer keeps water from flowing out under pressure even after the passage of a long period of time to exhibit excellent absorbency, and also has an anti-caking property under conditions of high temperature and high humidity to improve storage stability, is provided. The superabsorbent polymer composition of the present invention may be used to improve physical properties of a variety of diapers, potty training pants, incontinence pads, etc., thereby being applied to production of personal absorbent (Continued)

hygiene products having high absorbency and excellent storage stability under conditions of high temperature and high humidity.

10 Claims, 1 Drawing Sheet

(51) Int. Cl.
*A61L 15/24* (2006.01)
*C08L 33/04* (2006.01)
*C08K 3/22* (2006.01)

(56) References Cited

U.S. PATENT DOCUMENTS

| | | | |
|---|---|---|---|
| 4,734,478 A | 3/1988 | Tsubakimoto et al. | |
| 4,758,617 A | 7/1988 | Tanioku et al. | |
| 4,771,105 A * | 9/1988 | Shirai | A61L 15/60 525/330.1 |
| 5,002,986 A | 3/1991 | Fujiura et al. | |
| 5,140,076 A | 8/1992 | Hatsuda et al. | |
| 5,164,459 A * | 11/1992 | Kimura | A61L 15/60 525/329.5 |
| 5,728,742 A | 3/1998 | Staples et al. | |
| 6,124,391 A | 9/2000 | Sun et al. | |
| 6,436,418 B1 * | 8/2002 | Sheldon | A61F 13/8405 424/402 |
| 6,831,122 B2 | 12/2004 | Daniel et al. | |
| 2004/0077796 A1 | 4/2004 | Daniel et al. | |
| 2004/0214499 A1 | 10/2004 | Qin et al. | |
| 2008/0234645 A1 | 9/2008 | Dodge et al. | |
| 2009/0105389 A1 * | 4/2009 | Walden | C08L 101/14 524/437 |
| 2009/0182294 A1 | 7/2009 | Ikeuchi et al. | |
| 2010/0041550 A1 | 2/2010 | Riegel et al. | |
| 2012/0091392 A1 | 4/2012 | Daniel et al. | |
| 2012/0309619 A1 | 12/2012 | Kwon et al. | |
| 2013/0274405 A1 | 10/2013 | Tanabiki et al. | |
| 2016/0235882 A1 | 8/2016 | Noh et al. | |
| 2016/0361704 A1 | 12/2016 | Won et al. | |

FOREIGN PATENT DOCUMENTS

| | | |
|---|---|---|
| CN | 103339191 A | 10/2013 |
| EP | 0233067 A2 | 8/1987 |
| JP | 56-161408 A | 12/1981 |
| JP | S57158209 A | 9/1982 |
| JP | 57-198714 A | 12/1982 |
| JP | S5980459 A | 5/1984 |
| JP | S61257235 A | 11/1986 |
| JP | S63270741 | 11/1988 |
| JP | S6456707 A | 3/1989 |
| JP | H02227435 A | 9/1990 |
| JP | H0615574 B2 | 3/1994 |
| JP | H06107846 A | 4/1994 |
| JP | H07316337 A | 12/1995 |
| JP | 3121934 B2 | 1/2001 |
| JP | 2004517728 A | 6/2004 |
| JP | 2004261797 A | 9/2004 |
| JP | 2005097519 A | 4/2005 |
| JP | 2009534483 A | 9/2009 |
| JP | 2010502415 A | 1/2010 |
| JP | 6342510 B2 | 6/2018 |
| KR | 100614787 B1 | 8/2006 |
| KR | 20090123904 A | 12/2009 |
| KR | 20110049072 A | 5/2011 |
| KR | 20110092236 A | 8/2011 |
| KR | 20130120400 A | 11/2013 |
| WO | 03049778 A1 | 6/2003 |
| WO | 2004069293 A1 | 8/2004 |
| WO | 2004069915 A2 | 8/2004 |
| WO | 2012143215 A1 | 10/2012 |

OTHER PUBLICATIONS

Third Party Observation from PCT/KR2014/012213, dated Apr. 13, 2016.
Extended Search Report from European Application No. 14868927.6, dated Dec. 20, 2016.
Bowen P. Particle size distribution measurement from millimeters to nanometers and from rods to platelets. Journal of Dispersion Science and Technology. Jan. 11, 2020;23(5):631-62. (XP009102859).
Daijiten, Kagaku, "Aluminum hydroxide", Comprehensive Dictionary of Chemistry, vol. 5, Mar. 10, 1974, 6 pages (English translation of abtsract included only).
Notice of Opposition for Application No. EP 14868927.6 dated Jul. 22, 2019, pp. 1-7.
Satoshi Matsumoto, "Certified Experiment Results", Nippon Shokubai Co., Ltd., Superabsorbents Research Dept., Date of Experiment: Dec. 5, 2018 to Dec. 7, 2018, 4 pages.
Submission of the Proprietor during the Examination Proceedings dated Jul. 5, 2017.

* cited by examiner

[FIG. 1]
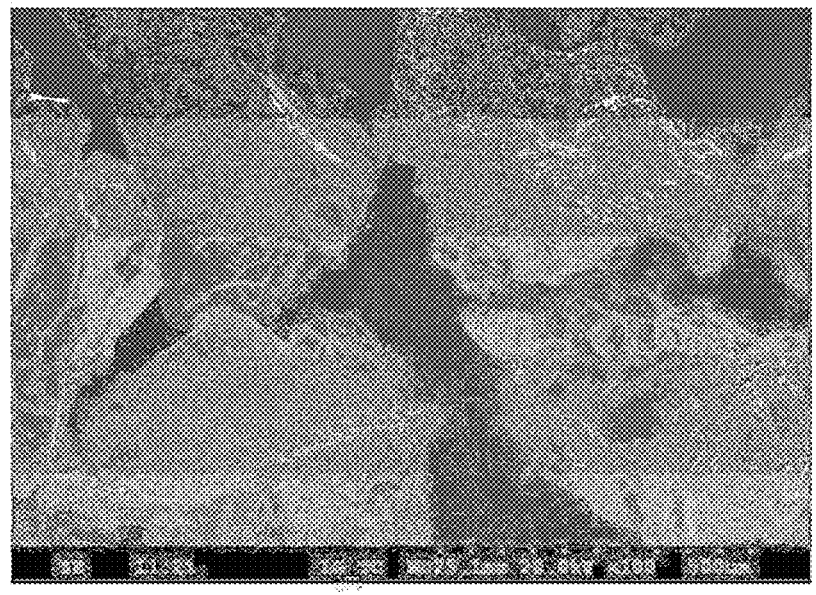
[FIG. 2]
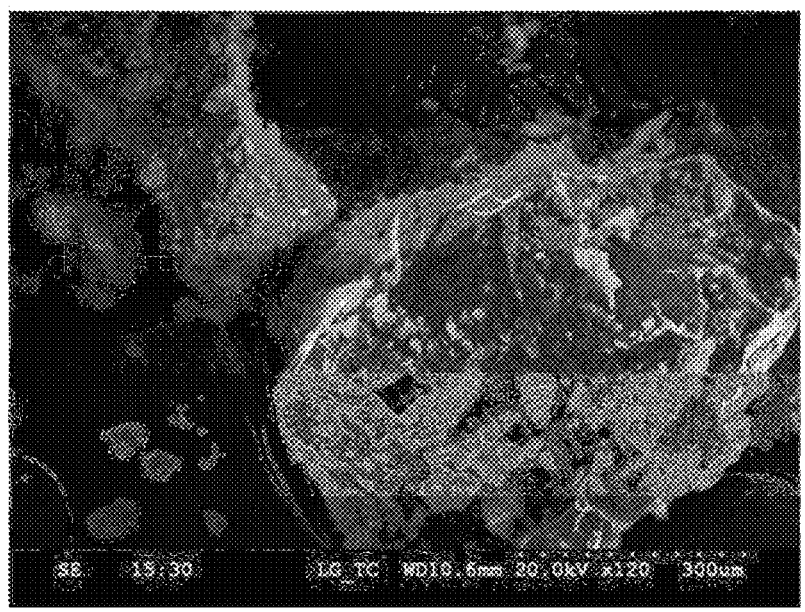

SUPERABSORBENT POLYMER COMPOSITION

CROSS-REFERENCE TO RELATED APPLICATION

This application is a national phase entry under 35 U.S.C. § 371 of International Application No. PCT/KR2014/012213, filed Dec. 11, 2014, which claims priority to Korean Patent Application No. 10-2013-0155597, filed Dec. 13, 2013, the disclosures of which are incorporated herein by reference.

TECHNICAL FIELD

The present invention relates to a superabsorbent polymer composition having an excellent anti-caking property under conditions of high temperature and high humidity, and high absorbency under pressure and excellent liquid permeability at the same time.

BACKGROUND OF THE INVENTION

A superabsorbent polymer (SAP) is a type of synthetic polymeric material capable of absorbing from 500 to 1000 times its own weight of moisture. Various manufacturers have denominated it with different names, such as SAM (Super Absorbency Material), AGM (Absorbent Gel Material), etc. Such superabsorbent polymers started to be practically applied in sanitary products, and they are now being widely used not only for hygiene products such as disposable diapers for children, etc., but also for water retaining soil products for gardening, water stop materials for the civil engineering and construction, sheets for raising seedling, fresh-keeping agents for food distribution fields, materials for poultices, or the like.

As a preparation process for such superabsorbent polymers, a process of reverse phase suspension polymerization and a process of solution polymerization have been known. For example, Japanese Patent Laid-open Publication Nos. S56-161408, S57-158209, and S57-198714 disclose the reverse phase suspension polymerization.

The process of solution polymerization further includes a thermal polymerization method in which a polymerization gel is polymerized while being broken and cooled in a kneader equipped with a plurality of shafts, and a photo-polymerization method in which an aqueous solution at a high concentration is irradiated with UV rays onto a belt to be polymerized and dried at the same time.

The water-containing gel polymers obtained through the polymerization reaction are generally marketed in a powdery form after drying and pulverization processes.

In the products made of superabsorbent polymers, permeability is an index for determining fluidity of a liquid to be absorbed. Permeability may differ depending on the properties such as particle size distribution of crosslinked polymers, particle shape, and the connectedness of the open pores between particles, and surface modification of the swollen gel. Fluidity of the liquid passing through swollen particles differs depending on permeability of the superabsorbent polymer composition. A liquid cannot flow readily through a superabsorbent polymer composition with low permeability.

As one of methods for increasing permeability of the superabsorbent polymer, there is a method of performing surface crosslinking reaction after polymerization, in which silica or clay is added together with a surface crosslinking agent. For example, U.S. Pat. Nos. 5,140,076 and 4,734,478 disclose the addition of silica during surface crosslinking of dry superabsorbent polymer powders.

However, while permeability is improved by the addition of silica or clay, there are problems that water retention capacity or absorbency under pressure is reduced in proportion thereto, and separation from the superabsorbent polymer easily occurs by external physical impact during transport. In particular, when silica or clay is mixed by a wet or dry process, an anti-caking property can be obtained, but absorbency under pressure is remarkably reduced. Therefore, it is difficult to achieve rapid absorption performance when practically applied to diapers, etc.

To ensure a desired anti-caking effect, silica must be mixed by a dry process. Even though a small amount thereof is added, absorption performance under pressure is excessively reduced. There is also a problem that dry mixed silica is separated from the superabsorbent polymer during transport in a line.

Accordingly, there is a need to develop a superabsorbent material which rapidly absorbs excretion, stores the excretion, or transfers the excretion to adjacent materials for distribution or storage in personal hygiene products such as diapers, and also has an excellent anti-caking property to show excellent storage stability under conditions of high temperature and high humidity.

DETAILS OF THE INVENTION

Objects of the Invention

The present invention is intended to provide a superabsorbent polymer composition which keeps water from flowing out under pressure even after the passage of a long period of time to show no reduction in absorbency under pressure (AUP) and that has excellent liquid permeability, and that also has an excellent anti-caking property under conditions of high temperature and high humidity to show excellent storage stability, and a personal absorbent hygiene product including the same.

Means for Achieving the Object

The present invention provides a superabsorbent polymer composition including a superabsorbent polymer and aluminum hydroxide, in which the aluminum hydroxide is attached on the surface of the superabsorbent polymer.

Further, the present invention provides a personal absorbent hygiene product including the superabsorbent polymer composition.

Hereinafter, a superabsorbent polymer composition and a personal absorbent hygiene product including the same will be described in more detail according to specific embodiments of the present invention. However, these are for illustrative purposes only, and the scope of the present invention is not intended to be limited thereby. It will be apparent to those skilled in the art that various modifications may be made thereto without departing from the scope of the invention.

Additionally, the term "including" or "containing" means that it includes a particular component (or particular element) without particular limitations unless otherwise mentioned in the entire present disclosure, and it cannot be interpreted as excluding the addition of the other components.

The present inventors studied a superabsorbent polymer composition and a personal absorbent hygiene product which have excellent initial absorbency and keep water from flowing out under pressure even after the passage of a long period of time so as to exhibit excellent absorbency, and as a result, they found that when surface treatment is performed using a predetermined aluminum hydroxide powder, a reduction in absorbency under pressure (AUP) may be minimized and excellent liquid permeability and anti-caking property may also be provided, thereby completing the present invention.

According to an aspect of the present invention, a superabsorbent polymer composition which has excellent liquid permeability without reduction in absorbency under pressure (AUP), and anti-caking property under conditions of high temperature and high humidity at the same time is provided. The superabsorbent polymer composition of the present invention includes a superabsorbent polymer and aluminum hydroxide, in which the aluminum hydroxide is attached on the surface of the superabsorbent polymer.

In particular, the superabsorbent polymer composition of the present invention is characterized in that it improves the anti-caking effect and permeability and also minimizes reduction in absorbency under pressure (AUP) by coating the surface of the superabsorbent polymer with particular aluminum hydroxide particles, as described below.

As used herein, the phrase "aluminum hydroxide attached on the surface of the superabsorbent polymer" means that about 70% by weight, about 90% by weight, or more of the aluminum hydroxide particles included in the superabsorbent polymer composition of the present invention are fixed on the surface of the superabsorbent polymer particles, and thus the aluminum hydroxide particles are not physically separated from the superabsorbent polymer particles in the composition. This state may be distinguished from a state in which the aluminum hydroxide particles are simply "mixed" with the superabsorbent polymer particles, and most of the aluminum hydroxide particles in the composition, for example, about 50% by weight or more thereof are physically separated from the superabsorbent polymer particles.

According to an embodiment of the present invention, the superabsorbent polymer composition may be in the form of a particle, and it may include a particular aluminum hydroxide powder and polymer resin particles.

Further, the superabsorbent polymer composition of the present invention may include aluminum hydroxide particles having a predetermined particle size, and therefore it may have improved liquid permeability without reduction in physical properties such as water retention capacity and absorbency under pressure, and may also have an anti-caking property under conditions of high temperature and high humidity to show improved storage stability.

The superabsorbent polymer composition of the present invention may provide a synergistic effect by a combination of physical properties of optimizing centrifuge retention capacity (CRC) and absorbency under pressure (AUP) at the same time. Therefore, the superabsorbent polymer composition of the present invention may induce excellent physical properties and a comfortable wearing sensation.

In the superabsorbent polymer composition, the centrifuge retention capacity (CRC) in the physiological saline solution may be 25 g/g or more, and the absorbency under pressure (AUP) of 0.7 psi in the physiological saline solution may be 10 g/g or more.

In the superabsorbent polymer composition, the centrifuge retention capacity (CRC) in the physiological saline solution may be represented by the following Equation 1:

$$CRC(g/g)=\{[W_2(g)-W_1(g)]/W_0(g)\}-1 \qquad \text{[Equation 1]}$$

wherein $W_0(g)$ is the weight (g) of the absorbent polymer composition, $W_1(g)$ is the weight of the apparatus, which is measured after draining water off at 250 G for 3 minutes (min) using a centrifuge without an absorbent polymer composition, and $W_2(g)$ is the weight of the apparatus including the absorbent polymer composition, which is measured after immersing the absorbent polymer composition in 0.9 wt % physiological saline solution at room temperature for 30 min and draining water off at 250 G for 3 min using a centrifuge.

In the superabsorbent polymer composition, the centrifuge retention capacity (CRC) in the physiological saline solution may be 25 g/g or more, preferably 28 g/g or more, and more preferably 30 g/g or more.

Further, in the superabsorbent polymer composition of the present invention, the absorbency under pressure (AUP) of 0.7 psi in the physiological saline solution may be represented by the following Equation 2:

$$AUP(g/g)=[W_4(g)-W_3(g)]/W_0(g) \qquad \text{[Equation 2]}$$

wherein $W_0(g)$ is the weight (g) of the absorbent polymer composition, $W_1(g)$ is the total weight of the absorbent polymer composition and the apparatus capable of providing a load for the absorbent polymer composition, and $W_2(g)$ is the total weight of the water-absorbed absorbent polymer composition after supplying water for the absorbent polymer composition under a load (0.7 psi) for 1 hour (h) and the apparatus capable of providing a load for the absorbent polymer composition.

In the superabsorbent polymer composition, its absorbency under pressure (AUP) of 0.7 psi in the physiological saline solution may be 10 g/g or more, preferably 15 g/g or more, and more preferably 20 g/g or more.

In the present invention, $W_0(g)$ described in Equations 1 to 2 corresponds to the weight (g) of the absorbent polymer, which is applied to each of the physical properties, and they may be the same as or different from each other.

In the superabsorbent polymer composition of the present invention, its free swell gel bed permeability (GBP) in the physiological saline solution may be 10 darcy or more, preferably 20 darcy or more, and more preferably 25 darcy or more. Herein, one darcy is the permeability of a solid through which one cubic centimeter of fluid, having a viscosity of one centipoise, will flow in one second through a section one centimeter thick and one square centimeter in cross-section, if the pressure difference between the two sides of the solid is one atmosphere. One darcy is equal to about $0.98692\times10^{-12}$ m$^2$ or about $0.98692\times10^{-8}$ cm$^2$.

Meanwhile, the superabsorbent polymer composition of the present invention is characterized in that it includes aluminum hydroxide particles having a specific particle size, together with the superabsorbent polymer. The aluminum hydroxide having an insolubility property is distributed and fixed on the surface of the superabsorbent polymer, thereby preventing aggregation of the superabsorbent polymer and improving the anti-caking effect and liquid permeability. The aluminum hydroxide is an inorganic substance which is insoluble in water and does not react with the superabsorbent polymer. In particular, since the aluminum hydroxide has a weight of about 40 times more than silica which is generally used as an anti-caking agent and has a high average particle size, a surface coating degree is relatively low, thereby minimizing the reduction in absorbency under pressure.

The aluminum hydroxide may have the average particle size of 2 μm to 50 μm, preferably 5 μm to 40 μm, and more preferably 7 μm to 20 μm. The aluminum hydroxide particles may have the average particle size of 5 μm or higher, in terms of minimizing the reduction in absorbency under pressure (AUP). Further, the aluminum hydroxide particles may have an average particle size of 50 μm or lower in order to prevent an increase in fine particle content and provide an anti-caking effect by fixing the aluminum hydroxide particles well on the surface of the superabsorbent polymer.

Further, in the superabsorbent polymer composition of the present invention, the aluminum hydroxide-treated superabsorbent polymer is additionally treated with a trace amount of silica, so free swell gel bed permeability (GBP) may be further improved. Silica may be additionally attached on the surface in an amount of 0.1 part by weight or less, based on 100 parts by weight of the superabsorbent polymer composition in which aluminum hydroxide is attached on the surface of the superabsorbent polymer. Preferably, the silica may be coated in an amount of 0.05 parts by weight or less on the surface of the aluminum hydroxide-treated superabsorbent polymer. In this regard, the free swell gel bed permeability (GBP) of the superabsorbent polymer composition in the physiological saline solution may be 65 darcy or more, preferably 70 darcy or more, and more preferably 75 darcy or more.

The superabsorbent polymer composition may have excellent vortex time, as well as excellent absorbency under pressure (AUP) and liquid permeability. The superabsorbent polymer composition may have a vortex time of 58 s or shorter, or 5 s to 58 s, preferably 53 s or shorter, and more preferably 50 s or shorter.

As described above, the superabsorbent polymer composition of the present invention keeps water from flowing out under pressure even after the passage of a long period of time to show no reduction in absorbency under pressure (AUP), exhibits good water permeability and vortex time, and also has an excellent anti-caking property at the same time. The anti-caking efficiency (A/C, anti-caking) of the superabsorbent polymer composition may be represented by the following Equation 3:

$$A/C(\%) = W_6(g)/W_5(g) \times 100 \qquad \text{[Equation 3]}$$

wherein $W_5(g)$ is the weight (g) of the superabsorbent polymer composition, and $W_6(g)$ is the weight of the absorbent polymer composition that has fallen, after evenly applying the composition on a 10 cm flask dish, placing it in a constant temperature and humidity chamber at a temperature of 40±3° C. and humidity of 70±3% for 10 min, and then inverting the flask dish on a filter paper and gently tapping the dish three times.

The superabsorbent polymer composition may have anti-caking efficiency (A/C, anti-caking) of 30% or more, preferably 60% or more, and more preferably 70% or more.

Meanwhile, the superabsorbent polymer (SAP) is a type of synthetic polymeric material capable of absorbing from 500 to 1000 times its own weight of moisture. Various manufacturers have denominated it with different names, such as SAM (Super Absorbency Material), AGM (Absorbent Gel Material), etc. Such superabsorbent polymers started to be practically applied in sanitary products, and they are now being widely used not only for hygiene products such as disposable diapers for children, etc., but also for water retaining soil products for gardening, water stop materials for the civil engineering and construction, sheets for raising seedling, fresh-keeping agents for food distribution fields, materials for poultices, or the like.

According to an embodiment of the present invention, the superabsorbent polymer may provide a synergistic effect by a combination of physical properties of optimizing centrifuge retention capacity (CRC), absorbency under pressure (AUP), and liquid permeability (GBP) at the same time. Herein, the centrifuge retention capacity (CRC), and absorbency under pressure (AUP), and liquid permeability (GBP) of the superabsorbent polymer may be equal to or higher than those described in the above composition.

In the superabsorbent polymer composition of the present invention, as shown in a scanning electron microscopy (SEM) image of FIG. 1, aluminum hydroxide is found to be distributed and fixed well onto the surface of the superabsorbent polymer according to the present invention. In contrast, as shown in a scanning electron microscopy (SEM) image of FIG. 2, when silica is mixed, a part of the silica agglomerates and is separated from the superabsorbent polymer. In this regard, the superabsorbent polymer composition of the present invention is characterized in that it has a particle size distribution ratio of less than 150 μm which is equal to or lower than that of the superabsorbent polymer used as the base polymer.

The superabsorbent polymer may include a crosslinked polymer which is obtained by surface crosslinking of a powdery base polymer using a diol or glycol-based compound having 2 to 8 carbon atoms, in which the powdery base polymer is prepared by polymerizing water-soluble ethylene-based unsaturated monomers having acidic groups which are at least partially neutralized.

In addition, since the crosslinking density of the crosslinked polymer may be a factor that affects the absorbency under pressure (AUP), the base polymer is preferably surface-crosslinked according to the method of the present invention.

The water-soluble ethylene-based unsaturated monomer may include one or more selected from the group consisting of an anionic monomer such as acrylic acid, methacrylic acid, maleic anhydride, fumaric acid, crotonic acid, itaconic acid, 2-acryloylethane sulfonic acid, 2-methacryloylethane sulfonic acid, 2-(meth)acryloylpropane sulfonic acid, or 2-(meth)acrylamide-2-methyl propane sulfonic acid, and salts thereof; a nonionic hydrophilic monomer such as (meth)acrylamide, N-substituted (meth)acrylate, 2-hydroxyethyl(meth)acrylate, 2-hydroxypropyl(meth)acrylate, methoxy polyethylene glycol (meth)acrylate, or polyethylene glycol(meth)acrylate; and an amino group-containing unsaturated monomer such as (N,N)-dimethylaminoethyl (meth)acrylate or (N,N)-dimethylaminopropyl(meth)acrylate, and a quaternary compound thereof.

As described above, the superabsorbent polymer composition of the present invention may have improved liquid permeability without reduction in physical properties such as water retention capacity and absorbency under pressure, and may also have the anti-caking property under conditions of high temperature and high humidity to show excellent storage stability. In particular, when a representative anti-caking agent, silica, is added in a very small amount of less than 0.1%, a reduction in absorbency under pressure (AUP) of 20% or more occurs, separation occurs due to a weight difference during processing, and fine powder is generated and adsorbed onto a filter, leading to loss of the added silica. Accordingly, there is a problem that the anti-caking effect is reduced. However, although aluminum hydroxide is added, for example, in an amount of 3% or more according to the present invention, the reduction in absorbency under pressure (AUP) is as low as 10% or less, there is no risk of loss during processing, and performance is stable despite a change in the content. Therefore, it is possible to easily prepare the superabsorbent polymer and to secure high quality and stability.

According to an embodiment of the present invention, as a method of attaching aluminum hydroxide to the superabsorbent polymer, various methods may be applied, in addition to a dry mixing method. For example, many methods are possible, such as a method of dispersing aluminum hydroxide in a surface treatment solution, a method of performing surface treatment after dry mixing aluminum hydroxide with the base polymer, a method of injecting aluminum hydroxide and the surface treatment solution at the same time, and a method of treating an aluminum hydroxide slurry. All these various methods are possible, because aluminum hydroxide is fixed due to viscosity generated when the superabsorbent polymer contacts a small amount of water. Silica may also be treated by any method.

However, when a method other than the dry method is performed, the anti-caking effect is reduced. In particular, no anti-caking effect is obtained when a composition or process requiring contact with lower alcohols such as methanol is employed. In any method, addition of a small amount of silica excessively reduces the AUP.

According to another aspect of the present invention, a personal absorbent hygiene product including the above described superabsorbent polymer composition is provided. The personal absorbent hygiene product of the present invention may include the superabsorbent polymer composition, a liquid permeable top sheet, and a waterproof back sheet.

In the personal absorbent hygiene product according to the present invention, the superabsorbent polymer composition has the above-described properties and includes the superabsorbent polymer and aluminum hydroxide, in which the aluminum hydroxide is attached on the surface of the superabsorbent polymer.

The liquid permeable top sheet generally has a soft feel, and is non-irritating to the wearer's skin. In particular, the top sheet must have a property of permitting liquid excretions to readily penetrate through the absorbent. A suitable top sheet having this property may be manufactured from a wide range of materials such as apertured plastic films, natural fibers, synthetic fibers, or a combination of natural and synthetic fibers.

Further, the waterproof back sheet is impermeable to liquid and thus prevents body excretions absorbed in the absorbent from contaminating or wetting products directly contacting the diaper, such as the wearer's clothes or bed sheets. Preferably, the back sheet is impermeable to liquid but permeable to gas. A general plastic film has been used in the back sheet having this property, and recently, a polyethylene film-laminated non-woven fabric has been used.

In addition to the above description, additions or subtractions are possible in the present invention, if necessary, and there is no particular limitation in the present invention.

Effects of the Invention

According to the present invention, a superabsorbent polymer composition which has improved liquid permeability without reduction in physical properties such as water retention capacity and absorbency under pressure (AUP), and also has anti-caking property under conditions of high temperature and high humidity to exhibit excellent storage stability at the same time by performing surface treatment using predetermined aluminum hydroxide particles is provided.

In particular, the superabsorbent polymer composition of the present invention may be used to improve physical properties of a variety of diapers, potty training pants, incontinence pads, etc., thereby being applied to production of personal absorbent hygiene products having high absorbency, to which an ultra-thin technology is applied.

BRIEF DESCRIPTION OF THE DRAWINGS

FIG. 1 is an image of a superabsorbent polymer surface-treated with aluminum hydroxide according to Example 6 of the present invention; and FIG. 2 is an image of a superabsorbent polymer surface-treated with silica according to Comparative Example 5 of the present invention.

DETAILED DESCRIPTION OF THE EMBODIMENT

Hereinafter, the preferred examples are provided for better understanding. However, the following examples are for illustrative purposes only, and the present invention is not intended to be limited by these examples.

EXAMPLE

Preparation Example: Preparation of Superabsorbent Polymer

First, a superabsorbent polymer was prepared as follows. A monomer aqueous solution having a monomer concentration of 45% by weight was prepared by mixing 100 g of acrylic acid, 0.25 to 0.5 of polyethylene glycol diacrylate (Mw=523) as a crosslinking agent, 83.3 g of 50% caustic soda (NaOH), and 89.8 g of water.

Subsequently, 810 g of the monomer aqueous solution was mixed with 30.54 g of a 0.18% ascorbic acid solution and 33 g of a 1% sodium persulfate solution, and the mixture was fed through a feed section of a continuous polymerization reactor with a kneader, together with 30.45 g of a 0.15% hydrogen peroxide solution, so as to perform polymerization. At this time, temperature of the reactor was maintained at 80° C., the maximum polymerization temperature was 110° C., and the polymerization time was 1 min and 15 seconds(s). Thereafter, kneading was continuously performed, and polymerization and kneading were performed for 20 min. The polymers having a size of 0.2 cm or less were thus distributed. At this time, the water content of the water-containing gel polymer finally formed was 51% by weight.

Subsequently, the water-containing gel polymer was dried with a hot air dryer at 180° C. for 30 min, and the dried water-containing gel polymer was pulverized with a pin mill. Next, the polymer was classified into a polymer having a particle size (average particle size) of less than 150 μm and a polymer having a particle size of 150 μm to 850 μm by using a sieve to obtain a base polymer (A) having CRC of 34 g/g and a base polymer (B) having CRC of 40 g/g.

Example 1

The base polymer (A) having CRC of 34 g/g was mixed with 0.5% by weight of 8 μm aluminum hydroxide by a dry method, and then a surface treatment solution containing 5% by weight of 1,3-propanediol was sprayed thereon to perform surface treatment of the superabsorbent polymer. Further, in the surface treatment step, the classified water-containing gel polymers were fed to one surface crosslinking reactor, and then surface crosslinking reaction of the water-containing gel polymers was performed at 180° C. or higher for 40 min.

Example 2

The base polymer (A) having CRC of 34 g/g was mixed with 1.0% by weight of 8 μm aluminum hydroxide by a dry method, and then a surface treatment solution containing 5% by weight of 1.3-propanediol was sprayed thereon to perform surface treatment of the superabsorbent polymer. Further, in the surface treatment step, the classified water-containing gel polymers were fed to one surface crosslinking reactor, and then surface crosslinking reaction of the water-containing gel polymers was performed at 180° C. or higher for 40 min.

Example 3

The base polymer (B) having CRC of 40 g/g was mixed with 1.0% by weight of 2 μm aluminum hydroxide by a dry method, and then a surface treatment solution containing 3% by weight of ethylene glycol diglycidyl ether was sprayed thereon to perform surface treatment of the superabsorbent polymer. Further, in the surface treatment step, the classified water-containing gel polymers were fed to one surface crosslinking reactor, and then surface crosslinking reaction of the water-containing gel polymers was performed at 120° C. or higher for 40 min.

Example 4

The base polymer (A) having CRC of 34 g/g was mixed with 1.5% by weight of 8 μm aluminum hydroxide by a dry method, and then a surface treatment solution containing 5% by weight of 1.3-propanediol was sprayed thereon to perform surface treatment of the superabsorbent polymer. Further, in the surface treatment step, the classified water-containing gel polymers were fed to one surface crosslinking reactor, and then surface crosslinking reaction of the water-containing gel polymers was performed at 180° C. or higher for 40 min.

Example 5

The base polymer (B) having CRC of 40 g/g was mixed with 1.5% by weight of 8 μm aluminum hydroxide by a dry method, and then a surface treatment solution containing 3% by weight of ethylene glycol diglycidyl ether was sprayed thereon to perform surface treatment of the superabsorbent polymer. Further, in the surface treatment step, the classified water-containing gel polymers were fed to one surface crosslinking reactor, and then surface crosslinking reaction of the water-containing gel polymers was performed at 120° C. or higher for 60 min.

Example 6

The base polymer (B) having CRC of 40 g/g was mixed with 2.0% by weight of 2 μm aluminum hydroxide by a dry method, and then a surface treatment solution containing 3% by weight of ethylene glycol diglycidyl ether was sprayed thereon to perform surface treatment of the superabsorbent polymer. Further, in the surface treatment step, the classified water-containing gel polymers were fed to one surface crosslinking reactor, and then surface crosslinking reaction of the water-containing gel polymers was performed at 120° C. or higher for 60 min.

Example 7

The base polymer (A) having CRC of 34 g/g was mixed with 3.0% by weight of 8 μm aluminum hydroxide by a dry method, and then a surface treatment solution containing 5% by weight of 1.3-propanediol was sprayed thereon to perform surface treatment of the superabsorbent polymer. Further, in the surface treatment step, the classified water-containing gel polymers were fed to one surface crosslinking reactor, and then surface crosslinking reaction of the water-containing gel polymers was performed at 180° C. or higher for 40 min.

Example 8

The base polymer (B) having CRC of 40 g/g was mixed with 3.0% by weight of 8 μm aluminum hydroxide by a dry method, and then a surface treatment solution containing 3% by weight of ethylene glycol diglycidyl ether was sprayed thereon to perform surface treatment of the superabsorbent polymer. Further, in the surface treatment step, the classified water-containing gel polymers were fed to one surface crosslinking reactor, and then surface crosslinking reaction of the water-containing gel polymers was performed at 120° C. or higher for 60 min.

Example 9

The base polymer (B) having CRC of 40 g/g was mixed with 3.0% by weight of 8 μm aluminum hydroxide by a dry method, and then a surface treatment solution containing 3% by weight of ethylene glycol diglycidyl ether was sprayed thereon to perform surface treatment of the superabsorbent polymer. Further, in the surface treatment step, the classified water-containing gel polymers were fed to one surface crosslinking reactor, and then surface crosslinking reaction of the water-containing gel polymers was performed at 120° C. or higher for 60 min. A 0.1% silica (Aerosil 200) was then mixed therewith by a dry method.

Example 10

The base polymer (B) having CRC of 40 g/g was mixed with 5.0% by weight of 8 μm aluminum hydroxide by a dry method, and then a surface treatment solution containing 3% by weight of ethylene glycol diglycidyl ether was sprayed thereon to perform surface treatment of the superabsorbent polymer. Further, in the surface treatment step, the classified water-containing gel polymers were fed to one surface crosslinking reactor, and then surface crosslinking reaction of the water-containing gel polymers was performed at 120° C. or higher for 60 min.

Comparative Example 1

A surface treatment solution containing 5% by weight of 1.3-propanediol was sprayed onto the base polymer (A) having CRC of 34 g/g to perform surface treatment of the superabsorbent polymer. Further, in the surface treatment step, the classified water-containing gel polymers were fed to one surface crosslinking reactor, and then surface crosslinking reaction of the water-containing gel polymers was performed at 180° C. or higher for 40 min.

Comparative Example 2

A surface treatment solution containing 3% by weight of ethylene glycol diglycidyl ether was sprayed onto the base polymer (B) having CRC of 40 g/g to perform surface treatment of the superabsorbent polymer. Further, in the surface treatment step, the classified water-containing gel polymers were fed to one surface crosslinking reactor, and then surface crosslinking reaction of the water-containing gel polymers was performed at 120° C. or higher for 60 min.

Comparative Example 3

The product obtained in Comparative Example 2 was mixed with 0.1% silica (Aerosil 200) having an average particle size of 12 nm by a dry method.

Comparative Example 4

The product obtained in Comparative Example 1 was mixed with 1.0% silica (Aerosil 200) having an average particle size of 12 nm by a dry method.

Comparative Example 5

The product obtained in Comparative Example 2 was mixed with 1.0% silica (Aerosil 200) having an average particle size of 12 nm by a dry method.

Experimental Example

Physical properties of the superabsorbent polymer compositions prepared in Examples 1 to 10 and Comparative Examples 1 to 5 were evaluated as follows, and the physical properties thus measured are shown in the following Table 1.

a) CRC: measured in accordance with WSP 241.3.10.
b) AUP: measured in accordance with WSP 242.3.10.
c) GBP: measured in accordance with a free swell gel bed permeability test described in Korean Patent Publication No. 10-2009-0123904.
d) A/C: the weight ($W_6$) of the superabsorbent polymer that had fallen was measured, after evenly applying 2 g of the superabsorbent polymer ($W_5$) on a 10 cm flask dish, placing it in a constant temperature and humidity chamber at a temperature of 40±3° C. and humidity of 70±3% for 10 min, and then inverting the flask dish on a filter paper and gently tapping the dish. The anti-caking efficiency (A/C, %) was calculated by $W_6/W_5 \times 100$, and a higher value indicates higher efficiency.
e) Vortex time: 50.0±1.0 mL of a 0.9% NaCl solution were added into a 100 mL beaker. A cylindrical stirrer bar (30×6 mm) was added and the saline solution was stirred on a stir plate at 600 rpm. 2.000±0.010 g of water-absorbent polymer particles were added to the beaker as quickly as possible, while starting a stop watch as addition began. The stopwatch was stopped when the surface of the mixture became "still", which means the surface has no turbulence, and while the mixture may still turn, the entire surface of particles turns as a unit. The displayed time of the stopwatch was recorded as vortex time.

TABLE 1

| | Base polymer* | 8 μm Al(OH)$_3$ content | 2 μm Al(OH)$_3$ content | Silica content | CRC (g/g) | AUP (g/g) | GBP (Darcy) | A/C (%) | Vortex time (sec) | Particle size distribution ratio of less than 150 μm (%) |
|---|---|---|---|---|---|---|---|---|---|---|
| Comparative Example 1 | A | — | — | — | 28.6 | 23.2 | 5 | 6 | 60 | 2.6 |
| Comparative Example 2 | B | — | — | — | 32.0 | 23.7 | 2 | 9 | 58 | 1.5 |
| Comparative Example 3 | B | — | — | 0.1 | 32.1 | 18.8 | 18 | 65 | 57 | 1.5 |
| Comparative Example 4 | A | — | — | 1.0 | 27.8 | 17.3 | 62 | 100 | 55 | 3.2 |
| Comparative Example 5 | B | — | — | 1.0 | 31.2 | 17.0 | 58 | 100 | 56 | 2.1 |
| Example 1 | A | 0.5 | — | — | 28.3 | 23.1 | 12 | 38 | 58 | 2.2 |
| Example 2 | A | 1.0 | — | — | 28.3 | 22.8 | 14 | 67 | 52 | 2.6 |
| Example 3 | B | — | 1.0 | — | 31.8 | 22.4 | 9 | 64 | 50 | 1.3 |
| Example 4 | A | 1.5 | — | — | 28.1 | 22.5 | 15 | 97 | 46 | 2.3 |
| Example 5 | B | 1.5 | — | — | 31.6 | 23.3 | 10 | 87 | 48 | 1.6 |
| Example 6 | B | — | 2.0 | — | 30.3 | 20.3 | 12 | 85 | 46 | 1.5 |
| Example 7 | A | 3.0 | — | — | 28.4 | 21.1 | 29 | 100 | 47 | 2.9 |
| Example 8 | B | 3.0 | — | — | 31.5 | 22.8 | 26 | 100 | 45 | 1.4 |
| Example 9 | B | 3.0 | — | 0.1 | 31.4 | 18.7 | 78 | 100 | 46 | 1.5 |
| Example 10 | B | 5.0 | — | — | 29.4 | 20 | 32 | 100 | 42 | 2.4 |

*Base polymer A: CRC 34 g/g, base polymer B: CRC 40 g/g

Further, FIGS. 1 and 2 are images of superabsorbent polymer surfaces treated with aluminum hydroxide or silica according to Example 6 and Comparative Example 5. As shown in FIG. 1, when the superabsorbent polymer was treated with 2.0% aluminum hydroxide according to Example 6, aluminum hydroxide was distributed well on the surface and strongly fixed thereon. In contrast, as shown in FIG. 2, when the superabsorbent polymer was treated with 1% silica by a dry method according to Comparative Example 5, it agglomerated unevenly and was even separated from the superabsorbent polymer. The separated silica particles are problematic in that they generate dust during transport.

As shown in FIG. 1, the superabsorbent polymer compositions of Examples 1 to 10 according to the present invention have an anti-caking property under conditions of high temperature and high humidity to improve storage stability, and also have excellent liquid permeability and vortex time, compared to those of Comparative Examples 1 to 2. Further, the superabsorbent polymer compositions of Examples 7 to 10 have an anti-caking property under conditions of high temperature and high humidity and liquid permeability which are equivalent to or higher than those of Comparative Examples 3 to 5, and also have high absorbency under pressure (AUP) and an excellent vortex time.

Further, the superabsorbent polymer compositions of Examples 1 to 9 showed a particle size distribution ratio of less than 150 μm, which is equivalent to or lower than those of Comparative Examples 1 to 2 which were not treated with aluminum hydroxide, suggesting that aluminum hydroxide was strongly attached to the base polymer, superabsorbent polymer. In contrast, the superabsorbent polymers of Comparative Examples 4 to 5 which were treated with 1% silica by a dry method showed a particle size distribution ratio of less than 150 μm, which is remarkably higher than the base polymer superabsorbent polymers of Comparative Examples 1 to 2, indicating very poor anti-caking performance.

In particular, when silica is treated by the dry method as in Comparative Examples 3 to 4, the anti-caking effect is improved, but excessive reduction in absorbency under pressure (AUP) was observed even by addition of a small amount of silica. Further, as in FIG. 2 and Examples 4 to 5 showing a separation of silica from the superabsorbent polymer and an increase in the amount passed through 150 μm, the anti-caking property may be reduced by separation due to the weight difference during transport of products prepared by simply mixing the superabsorbent polymer with silica, and loss and non-uniform distribution of silica due to bag filter collection, and a large amount of dust may also be generated to deteriorate work environments. It is apparent that the anti-caking property may also be reduced when a wet treatment is performed in order to fix silica on the polymer surface, and in particular, efficiency is dramatically reduced when the surface treatment solution is used together with alcohols.

The invention claimed is:

1. A superabsorbent polymer composition comprising: a superabsorbent polymer and particles, wherein the particles are attached on a surface of the superabsorbent polymer, wherein the particles consist of aluminum hydroxide particles having an average particle size of 2 μm to 50 μm, and wherein 70% by weight or more of the aluminum hydroxide particles included in the superabsorbent polymer is fixed on the surface of the superabsorbent polymer, wherein an anti-caking efficiency (A/C) of the superabsorbent polymer composition is 30% or more, wherein the anti-caking efficiency is represented by the following equation 3:

$$A/C(\%) = W_6(g)/W_5(g) \times 100 \quad \text{(Equation 3)}$$

wherein $W_5(g)$ is the weight (g) of the superabsorbent polymer composition, and $W_6(g)$ is the weight of the absorbent polymer composition that has fallen, after evenly applying the superabsorbent composition on a 10 cm flask dish, placing it in a constant temperature and humidity chamber at a temperature of 40±3° C. and humidity of 70±3% for 10 min, and then inverting the flask dish on a filter paper and gently tapping the dish three times.

2. The superabsorbent polymer composition of claim 1, comprising the aluminum hydroxide particles in an amount of 0.5 to 5 parts by weight, based on 100 parts by weight of the superabsorbent polymer.

3. The superabsorbent polymer composition of claim 1, comprising a crosslinked polymer which is obtained by surface crosslinking of a powdery base polymer using a diol or glycol-based compound having 2 to 8 carbon atoms, wherein the powdery base polymer is prepared by polymerizing water-soluble ethylene-based unsaturated monomers having acidic groups which are at least partially neutralized.

4. The superabsorbent polymer composition of claim 3, wherein the water-soluble ethylene-based unsaturated monomer comprises one or more selected from the group consisting of an anionic monomer, a nonionic hydrophilic monomer, or an amino group-containing unsaturated monomer, wherein the anionic monomer comprises acrylic acid, methacrylic acid, maleic anhydride, fumaric acid, crotonic acid, itaconic acid, 2-acryloylethane sulfonic acid, 2-methacryloylethane sulfonic acid, 2-(meth)acryloylpropane sulfonic acid, or 2-(meth)acrylamide-2-methyl propane sulfonic acid, or salts thereof; wherein the nonionic hydrophilic monomer comprises (meth)acrylamide, N-substituted (meth)acrylate, 2-hydroxyethyl(meth)acrylate, 2-hydroxypropyl(meth)acrylate, methoxy polyethylene glycol (meth) acrylate, or polyethylene glycol (meth)acrylate; and wherein the amino group-containing unsaturated monomer comprises (N,N)-dimethylaminoethyl(meth)acrylate or (N,N)-dimethylaminopropyl(meth)acrylate, or a quaternary compound thereof.

5. The superabsorbent polymer composition of claim 1, wherein the superabsorbent polymer composition is in the form of particles.

6. The superabsorbent polymer composition of claim 1, wherein centrifuge retention capacity (CRC) in a physiological saline solution is 25 g/g or more.

7. The superabsorbent polymer composition of claim 1, wherein absorbency under pressure (AUP) of 0.7 psi in a physiological saline solution is 20 g/g or more.

8. A personal absorbent hygiene product comprising the superabsorbent polymer composition of claim 1.

9. The personal absorbent hygiene product of claim 8, comprising the superabsorbent polymer composition, a liquid permeable top sheet, and a waterproof back sheet.

10. The superabsorbent polymer of claim 1, wherein the aluminum hydroxide particles consist of particles having the average particle size of 2 μm to 20 μm.

* * * * *